(12) United States Patent
Andreux et al.

(10) Patent No.: US 12,220,424 B2
(45) Date of Patent: *Feb. 11, 2025

(54) COMPOSITIONS COMPRISING NICOTINAMIDE RIBOSIDE AND A UROLITHIN

(71) Applicant: Amazentis SA, Lausanne (CH)

(72) Inventors: Penelope Andreux, Eclepens (CH); Christopher L. Rinsch, Lausanne (CH)

(73) Assignee: Amazentis SA, Lausanne (CH)

( * ) Notice: Subject to any disclaimer, the term of this patent is extended or adjusted under 35 U.S.C. 154(b) by 569 days.

This patent is subject to a terminal disclaimer.

(21) Appl. No.: 17/497,392

(22) Filed: Oct. 8, 2021

(65) Prior Publication Data

US 2022/0105117 A1 Apr. 7, 2022

Related U.S. Application Data

(63) Continuation of application No. 16/064,922, filed as application No. PCT/EP2016/082596 on Dec. 23, 2016, now Pat. No. 11,166,972.

(30) Foreign Application Priority Data

Dec. 24, 2015 (GB) ...................................... 1522892
Jul. 8, 2016 (GB) ...................................... 1611960

(51) Int. Cl.
| | | |
|---|---|---|
| *A61K 31/706* | (2006.01) | |
| *A23L 29/00* | (2016.01) | |
| *A23L 33/10* | (2016.01) | |
| *A61K 9/00* | (2006.01) | |
| *A61K 31/366* | (2006.01) | |
| *A61P 21/00* | (2006.01) | |
| *A61P 25/28* | (2006.01) | |

(52) U.S. Cl.
CPC ............ *A61K 31/706* (2013.01); *A23L 29/00* (2016.08); *A23L 33/10* (2016.08); *A61K 9/0053* (2013.01); *A61K 31/366* (2013.01); *A61P 21/00* (2018.01); *A61P 25/28* (2018.01); *A23V 2002/00* (2013.01); *A23V 2200/316* (2013.01); *A23V 2200/322* (2013.01); *A61K 2300/00* (2013.01)

(58) Field of Classification Search
None
See application file for complete search history.

(56) References Cited

U.S. PATENT DOCUMENTS 11,166,972 B2 11/2021 Rinsch et al.
2012/0164243 A1 6/2012 Rinsch et al.

FOREIGN PATENT DOCUMENTS

| WO | WO-2007/008548 A2 | 1/2007 |
|---|---|---|
| WO | WO-2014/111580 A1 | 7/2014 |
| WO | WO-2015/097231 A1 | 7/2015 |

OTHER PUBLICATIONS

Burattini et al., "C2C12 murine myoblasts as a model of skeletal muscle development: morpho-functional characterization," European Journal of Histochemistry, 48(3):223-234 (2004).
Chen et al., "Decreased heat shock protein 27 expression and altered autophagy in human cells harboring A8322G mitochondrial DNA mutation," Mitochondrion, 11:739-749 (2011).
Forterre et al., "Proteomic Analysis of C2C12 Myoblast and Myotube Exosome-Like Vesicles: A New Paradigm for Myoblast-Myotube Cross Talk?" PLoS One 9(1): e84153 (2014).
International Search Report for International Application No. PCT/EP2016/082596 mailed Apr. 2005.
Kahn et al., "Effective Treatment of Mitochondrial Myopathy by Nicotinamide Ribose, a Vitamin B3," Embo Molecular Medicine, vol. 6, (2014).
Peng et al., "Inhibiting cytosolic translation and autophagy improves health in mitochoncrial disease," Human Molecular Genetics, 24(17):4829-4847 (2015).
Tirziu et al., "Cell Communications in the Heart," Circulation, 122(9): 928-937 (2010).
Yuan et al., "Mitochondrial myopathy with autophagic vacuoles in patients with the m.8344A>G mutation," J Clin Pathol, 66:659-664 (2013).

*Primary Examiner* — Bahar Craigo
(74) *Attorney, Agent, or Firm* — Foley Hoag LLP; Dana M. Gordon; Lawrence P. Tardibono

(57) ABSTRACT

A composition comprising:
  a) nicotinamide riboside and
  b) a urolithin which is a compound of formula (I) or a salt thereof:

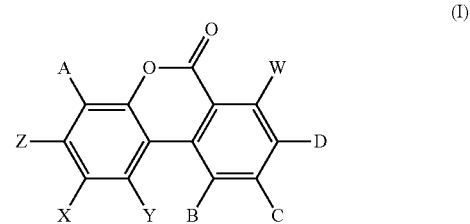

(I)

wherein:
A, B, C and D are each independently selected from H and OH;
W, X and Y are each independently selected from H and OH; and
Z is selected from H and OH.
The compositions are useful as medicaments, for example for treating muscle-related pathological conditions, neurodegenerative diseases, and/or mitochondrial diseases and as dietary supplements, functional foods and beverages, and specialised nutrition or medical foods.

10 Claims, 3 Drawing Sheets

COMPOSITIONS COMPRISING NICOTINAMIDE RIBOSIDE AND A UROLITHIN

RELATED APPLICATIONS

This application is a continuation of U.S. application Ser. No. 16/064,922, filed Jun. 21, 2018; which is the U.S. national phase of International Patent Application No. PCT/EP2016/082596, filed Dec. 23, 2016; which claims benefit to United Kingdom Application No. 1611960.4, filed Jul. 8, 2016; and United Kingdom Application No. 1522892.7, filed Dec. 24, 2015.

The current invention relates to nutritional and medical formulations of urolithins and nicotinamide riboside, in particular urolithin A and nicotinamide riboside. The formulations are especially useful to boost mitophagy and mitochondrial biogenesis simultaneously to promote optimal mitochondrial function.

BACKGROUND

Urolithins have been proposed as treatments of a variety of conditions related to inadequate mitochondrial activity, including obesity, reduced metabolic rate, metabolic syndrome, diabetes mellitus, cardiovascular disease, hyperlipidemia, neurodegenerative diseases, cognitive disorders, mood disorders, stress, and anxiety disorders; for weight management, or to increase muscle performance or mental performance. See WO2012/088519 (Amazentis SA). In WO2007/127263 (The Regents of the University of California), the use of urolithins for the treatment of various neoplastic diseases is described.

International patent publication WO2014/004902 (derived from application PCT/US2013/48310) discloses a method of increasing autophagy, including specifically mitophagy, in a cell, comprising contacting a cell with an effective amount of a urolithin or a pharmaceutically acceptable salt thereof, thereby increasing autophagy, including specifically mitophagy, in the cell. Administration may be to a subject having a disease or condition selected from metabolic stress, cardiovascular disease, endothelial cell dysfunction, sarcopenia, muscle degenerative disease, Duchenne muscular dystrophy, alcoholic liver disease, nonalcoholic fatty liver disease, drug-induced liver or muscle injury, α1-antitrypsin deficiency, ischemia/reperfusion injury, inflammation, aging of the skin, inflammatory bowel disease, Crohn's disease, obesity, metabolic syndrome, type II diabetes mellitus, hyperlipidemia, osteoarthritis, neurodegenerative disease, Alzheimer's disease, Huntington's disease, Parkinson's disease, amyotrophic lateral sclerosis, age-related macular degeneration, mitochondrial diseases (including for example poor growth, loss of muscle coordination, muscle weakness, visual problems, hearing problems, heart disease, liver disease, kidney disease, gastrointestinal disorders, respiratory disorders, neurological problems, autonomic dysfunction sometimes learning disabilities, and dementia as a result of mitochondrial disease), muscle diseases; cancer, cognitive disorder, stress, and mood disorder.

In particular, urolithins have been proposed as treatments for muscle-related pathological conditions. Muscle-related pathological conditions include myopathies and neuromuscular diseases. Examples of such conditions include Duchenne muscular dystrophy, acute sarcopenia, for example muscle atrophy and/or cachexia, for example associated with burns, bed rest, limb immobilization, or major thoracic, abdominal, neck and/or orthopedic surgery, amyotrophic lateral sclerosis and multiple sclerosis. Age-related muscle-loss is an especially prevalent condition. Cachexia due to prolonged immobilization or other diseases, for example cancer, are other conditions that are often characterised by poor muscle performance.

Effective muscle function and physical performance is important for having a high quality of life at all ages in healthy individuals as well as in those individuals suffering from a disease, especially the elderly. Improved muscle performance is of particular interest to athletes. For example an increase in muscular contraction strength, increase in amplitude of muscle contraction, or shortening of muscle reaction time between stimulation and contraction are all of benefit to individuals, especially athletes. For elderly suffering from age related decline in muscle function including muscle loss/wasting or individuals suffering from cachexia muscle wasting, an improvement in muscle and physical performance is important for basic aspects of daily functioning such as walking speed and distance they can walk unassisted.

Nicotinamide riboside is a form of vitamin B3 and a precursor of NAD+ which occurs naturally in yeast. It is known to induce mitochondrial biogenesis, and has been suggested as having benefits on muscle performance, metabolism, neuroprotection, healthy aging and cardiovascular health (see for example Chi and Sauve, *Curr Opin Clin Nutr Metab Care*, 2013, 16, 657-661, and Canto et al, *Cell Metabolism*, 2012, 15, 838-847).

Surprisingly, it has now been found that compositions which comprise both nicotinamide riboside and a urolithin demonstrate a synergistic effect, which could not have been predicted.

SUMMARY OF THE INVENTION

The present invention provides a composition comprising:
a) nicotinamide riboside; and
b) a compound of formula (I) or a salt thereof:

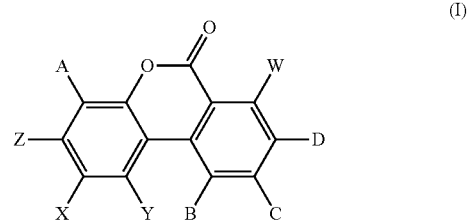

wherein:
A, B, C and D are each independently selected from H and OH;
W, X and Y are each independently selected from H and OH; and
Z is selected from H and OH.

Compounds of Formula (I) are members of the Urolithin family; in particular, the compound of Formula (I) is Urolithin A. The composition of the invention is useful in the treatment of diseases and conditions related to inadequate mitochondrial activity and/or low muscle mass or poor muscle performance, in the enhancement of muscle growth and/or muscle performance, and for various other purposes, as set out hereinbelow.

The composition of the invention finds use in improving muscle and/or physical performance, improving muscle function, preventing a decline in muscle function, increasing muscle mass and/or reducing muscle wasting. The improvement in muscle performance, improving muscle function, the increase in muscle mass and/or reduction in muscle wasting may be as part of a medical treatment, or it may be for personal preference ("lifestyle") or cosmetic reasons. The composition may for example be used to maintain a healthy state during aging. The compositions can be used as a dietary supplement, as a functional food, functional beverage, specialised nutrition product or as a medical food or medical nutrition product. The compositions of the invention can be for use as a medicament.

The invention further provides a composition of the invention for use in the treatment of muscle-related pathological conditions. The invention also provides a method of treating a muscle-related pathological condition in a subject comprising administering to the subject an effective amount of a composition of the invention. The invention provides a composition of the invention for use in enhancing muscle performance. The invention also provides a method of enhancing muscle performance by administering to a subject an effective amount of a composition of the invention.

In a treatment of the invention, it is not essential for the Urolithin and nicotinamide riboside to be administered simultaneously as part of a single composition. The invention also provides a method of treating a muscle-related pathological condition in a subject, or enhancing muscle function in a subject comprising administering to the subject an effective amount of a urolithin (for example Urolithin A) and an effective amount of nicotinamide riboside. The urolithin and the nicotinamide riboside can be administered at the same time or separated by a time interval. The invention further provides a kit comprising urolithin and nicotinamide riboside for use in such a method. The urolithin and nicotinamide riboside may be in different physical forms.

DETAILED DESCRIPTION

Nicotinamide Riboside:

Nicotinamide riboside is a pyridine-nucleoside form of vitamin B3 that functions as a precursor to NAD+. Its structure is shown in formula (II) below.

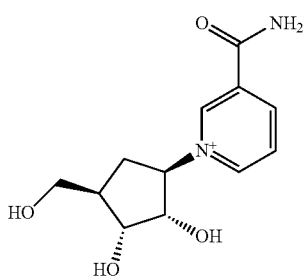

(II)

Nicotinamide riboside is secreted by yeast and is present as a trace nutrient in some food. It is available in supplement form (for example as its chloride salt, distributed by Chromadex under the tradename NIAGEN™)

Urolithins:

Urolithins are metabolites produced by the action of mammalian, including human, gut microbiota on ellagitannins and ellagic acid. Ellagitannins and ellagic acid are compounds commonly found in foods such as pomegranates, nuts and berries. Ellagitannins are minimally absorbed in the gut themselves. Urolithins are a class of compounds with the representative structure (I) shown above. The structures of some particularly common urolithins are described in the table below, with reference to structure (I).

|  | Substituent of structure (I) | | | | | |
| --- | --- | --- | --- | --- | --- | --- |
|  | A | B | C | D | W, X and Y | Z |
| Urolithin A | H | H | H | OH | H | OH |
| Urolithin B | H | H | H | H | H | OH |
| Urolithin C | H | H | OH | OH | H | OH |
| Urolithin D | OH | H | OH | OH | H | OH |
| Isourolithin A | H | H | OH | H | H | OH |
| Isourolithin B | H | H | OH | H | H | H |
| Urolithin M-5 | OH | OH | OH | OH | H | OH |
| Urolithin M-6 | H | OH | OH | OH | H | OH |
| Urolithin M-7 | H | OH | H | OH | H | OH |

In practice, for commercial scale products, it is convenient to synthesise the urolithins. Routes of synthesis are described, for example, in WO2014/004902.

Particularly suitable compounds for use in compositions of the invention are the naturally-occurring urolithins. Thus, Z is preferably OH and W, X and Y are preferably all H. When W, X and Y are all H, and A, and B are both H, and C, D and Z are all OH, then the compound is Urolithin C. When W, X and Y are all H, and A, B and C are all H, and D and Z are both OH, then the compound is Urolithin A. Preferably, the Urolithin used in a formulation of the invention is Urolithin A or Urolithin B or Urolithin C. More preferably, the urolithin used in a formulation of the invention is Urolithin A or Urolithin B. Most preferably, the Urolithin used in a formulation of the invention is Urolithin A.

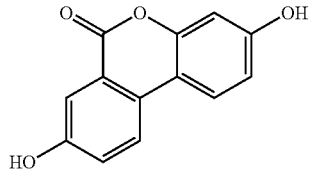

Urolithin A

Isourolithin A and B may also be mentioned. When W, X and Y are all H, and A, B and D are all H, and C and Z are both OH, then the compound is Iso-urolithin A. When W, X, Y and Z are all H, and A, B and D are all H, and C is OH, then the compound is Iso-urolithin B.

Preferably, urolithin for use in compositions of the invention is micronized. It has been found that micronized urolithin can be dissolved or suspended more rapidly and more effectively than unmicronised urolithin. Micronized urolithin preferably has a $D_{50}$ size of under 100 μm—that is to say that 50% of the urolithin by mass has a particle diameter size of under 100 μm. More preferably, the urolithin has a $D_{50}$ size of under 75 μm, for example under 50 μm, for example under 25 μm, for example under 20 μm, for example under 10 μm. More preferably, the urolithin has a $D_{50}$ in the range 0.5-50 μm, for example 0.5 to 20 μm, for example 0.5 to 10 μm, for example 1 to 10 μm. Preferably, the urolithin has a $D_{90}$ size of under 100 μm—that is to say that 90% of the urolithin by mass has a particle diameter size of under 100 μm. More preferably, the urolithin has a $D_{90}$ size of under 75 μm, for example under 50 μm, for example under 25 μm, for example under 20 μm, for example under 15 μm. The urolithin preferably has a $D_{90}$ in the range 5 to 100 μm, for example 5 to 50 μm, for example 5 to 20 μm. Micronisation can be achieved by methods established in the art, for example compressive force milling, hammermilling, universal or pin milling, or jet milling (for example spiral jet milling or fluidised-bed jet milling) may be used. Jet milling is especially suitable.

Dosing:

The effective amount of the composition to be taken will vary depending upon the manner of administration, the age, body weight, and general health of the subject. Factors such as the disease state, age, and weight of the subject may be important, and dosage regimens may be adjusted to provide the optimum response.

Conventional nicotinamide riboside supplements are generally taken at a level of 250 mg a day, but may be taken at higher doses. The daily dose nicotinamide riboside provided by compositions of the invention may be in the range of 20 to 5000 mg, for example 20 to 4000 mg, for example 200 to 4000 mg, for example 20 to 3000 mg, for example 20 to 2000 mg, for example 100 to 1000 mg, for example 100 to 800 mg, for example 200 to 600 mg, for example 200 to 400 mg, for example 200 to 300 mg, for example 250 mg. The daily intake of nicotinamide riboside may be provided as a single serving, or may be divided between multiple servings.

A unit dose may be in the form of a snack bar; a snack bar of weight 25 to 150 g, for example 40 to 100 g may contain the necessary amount of nicotinamide riboside (such as 200 to 300 mg of nicotinamide riboside, or another amount mentioned above). A unit dose composition may alternatively be in the form of a drink, for example provided in a container (for example a pouch or a bottle) of a volume suitable for a single dose (for example 50 to 500 ml, for example 100 to 300 ml). A drink of 100 to 300 ml may contain the necessary amount of nicotinamide riboside. A unit dose composition may alternatively be in the form of a powder to be reconstituted into a drink, for example a suitable quantity of powder for a single dose (for example 5 g to 10 g of powder, containing 200 to 300 mg of nicotinamide riboside). A reconstituted drink of 100 to 500 ml may contain the necessary amount of nicotinamide riboside. As mentioned below, a composition for use in the invention can take any suitable physical form. It may be in the form of a solid (for example a tablet or a bar), a semi-solid (for example a softgel, capsule (for example a hard capsule) or dragee), a powder or a liquid (including emulsions). The compositions of the invention may be nutritional compositions. The compositions of the invention may be pharmaceutical compositions. The compositions can be in the form of a dietary supplement, as a functional food, functional beverage, or as a medical food or medical nutrition product. Daily intake of the urolithin (for example Urolithin A) component is typically in the range of 10 mg to 5 g per day, for example 20 mg to 2500 mg per day, for example 25 mg to 250 mg, for example 25 mg to 500 mg, for example 50 mg to 1500 mg per day, for example 250 mg to 2000 mg, for example 250 mg to 1500 mg per day, for example 50 mg to 1000 mg per day, for example 20 mg to 250 mg per day, for example 250 mg to 1000 mg per day, for example 500 mg to 1000 mg per day, for example 750 mg to 1000 mg per day. In one embodiment, the composition is taken in an amount to provide a dosage of urolithin in the range from about 0.2 mg/kg/day to greater than about 100 mg/kg/day. For example, the dosage of urolithin may be 0.2 to 100, 0.2 to 50, 0.2 to 25, 0.2 to 10, 0.2 to 7.5, 0.2 to 5, 0.25 to 100, 0.25 to 25, 0.25 to 25, 0.25 to 10, 0.25 to 7.5, 0.25 to 5, 0.5 to 50, 0.5 to 25, 0.5 to 20, 0.5 to 15, 0.5 to 10, 0.5 to 7.5, 0.5 to 5, 0.75 to 50, 0.75 to 25, 0.75 to 20, 0.75 to 15, 0.75 to 10, 0.75 to 7.5, 0.75 to 5, 1.0 to 50, 1 to 25, 1 to 20, 1 to 15, 1 to 10, 1 to 7.5, 1 to 5, 2 to 50, 2 to 25, 2 to 20, 2 to 15, 2 to 10, 2 to 7.5, or 2 to 5 mg/kg/day.

A unit dose may be in the form of a snack bar; a snack bar of weight 25 to 150 g (for example 40 to 100 g) may contain the necessary amount of urolithin. A unit dose composition may alternatively be in the form of a drink, for example provided in a container (for example a pouch) of a volume suitable for a single dose (for example 100 to 300 ml). A drink of 50 to 500 ml (for example 100 to 300 ml) may contain the necessary amount of urolithin. A drink providing the composition of the invention may contain the urolithin at a concentration of 0.1 to 50 mg per ml, for example 0.5 to 10 mg per ml, for example 1 to 5 mg per ml. A unit dose may alternatively be in the form of one or more solids such as a compressed tablet. A single compressed tablet may contain a urolithin dose of, for example, 25 mg, 50 mg, 75 mg, 100 mg, 150 mg, 200 mg, 250 mg, 300 mg, 350 mg, 400 mg, 450 mg, 500 mg, 600 mg, 700 mg, 800 mg, 900 mg or 1000 mg. A unit dose may alternatively be in the form of one or more semi-solid doses, such as a softgel or paste. A single softgel capsule may contain a urolithin dose of, for example, 25 mg, 50 mg, 75 mg, 100 mg, 150 mg, 200 mg, 250 mg, 300 mg, 350 mg, 400 mg, 450 mg or 500 mg, for example 250 mg.

The weight ratio between the nicotinamide riboside component and the urolithin is generally in the range 500:1 to 1:250; for example 400:1 to 1:250; for example 300:1 to 1:250; for example 300:1 to 1:100; for example 200:1 to 1:100; for example 200:1 to 1:75; for example 200:1 to 1:50; for example 200:1 to 1:25; for example 50:1 to 1:20; for example 25:1 to 1:15; for example 10:1 to 1:10; for example 5:1 to 1:8; for example 5:1 to 1:5; for example 3:1 to 1:5; for example 1:1 to 1:8; for example 1:1 to 1:5; for example 1:2 to 1:6; for example 1:2 to 1:5; for example 1:3 to 1:4. The ratio may also be for example 1:3 to 5:1; for example 1:1 to 8:1; for example 1:1 to 5:1; for example 2:1 to 6:1; for example 2:1 to 5:1; for example 3:1 to 4:1.

A composition of the invention may thus contain 20 to 5000 mg of nicotinamide riboside and 10 mg to 5 g of urolithin; for example 20 to 4000 mg of nicotinamide riboside and 10 mg to 5 g of urolithin; for example 20 to 3000 mg of nicotinamide riboside and 10 mg to 5 g of urolithin; for example 20 to 2000 mg of nicotinamide riboside and 10 mg to 5 g of urolithin; for example 150 to 3000 mg of nicotinamide riboside and 10 mg to 5 g of urolithin; for example 50 mg to 500 mg nicotinamide riboside and 50 mg to 500 mg urolithin; for example 250 to 2000 mg of nicotinamide riboside and 10 to 3000 mg of urolithin; for example 300 to 3000 mg of nicotinamide riboside and 10 to 3000 mg of urolithin; for example 200 to 600 mg of nicotinamide riboside and 20 mg to 2500 mg of urolithin; for example 250 mg to 2500 mg of nicotinamide riboside and 100 mg to 2000 mg of urolithin; for example 200 to 400 mg of nicotinamide riboside and 20 mg to 2500 mg of urolithin; for example 200 to 300 mg of nicotinamide riboside and 50 mg to 1000 mg of urolithin; 200 to 300 mg of nicotinamide riboside and 50 mg to 500 mg of urolithin; 200 to 300 mg of nicotinamide riboside and 100 mg to 500 mg of urolithin. The compositions may further contain, for example, protein, carbohydrates, vitamins and minerals.

Doses of compounds are mentioned herein on a daily dose basis. In many cases, the beneficial effects of the compositions of the invention manifest themselves most when the composition has been taken for an extended period of time, for example 2 weeks or more, for example 4 weeks or more, for example 6 weeks or more, for example 8 weeks, for example 12 weeks or more, for example 16 weeks or more, for example 20 weeks or more, for examples 24 weeks or more.

Forms of Compositions:

The compositions of the invention can take any suitable physical form. They may be in the form of a solid (for example a tablet or a bar), a semi-solid (for example a softgel, capsule (for example a hard capsule) or dragee), a powder or a liquid (including emulsions). The compositions of the invention may be nutritional compositions. The compositions of the invention may be pharmaceutical compositions. The compositions can be in the form of a dietary supplement, as a functional food, functional beverage, or as a medical food or medical nutrition product.

Tablet form compositions may be of any suitable type, and they may contain excipients conventional in the art. The excipients can, for example, provide a desired hardness, shelf-life and flavour such that the compostion has an acceptable taste, an attractive appearance and good storage stability. A bar may be of any suitable type and it may contain ingredients conventionally used for the preparation of snack bars.

Semi-solid forms may likewise contain excipients conventional in the art. The excipients can, for example, provide a desired hardness, shelf-life and flavour such that the composition has an acceptable taste, an attractive appearance and good storage stability. Semi-solid forms may be provided for oral administration, or for topical administration.

Powders are commonly used for the supply of nutritional and medical compositions. Powders have the advantage that multiple doses can be provided in a single container, and doses of various sizes can be used from the same supplied container. Powders generally have good storage properties. Powder compositions may also contain excipients conventional in the art. The excipients can, for example, provide a shelf-life, flavour and moisture resistance such that the composition has an acceptable taste, an attractive appearance and good storage stability. The current invention may take the form of a kit comprising a nicotinamide riboside composition together with a separate composition containing urolithin, for example nicotinamide riboside powder composition together with a separate solid or liquid composition containing urolithin. A solid or liquid composition containing urolithin (for example a tablet or a drink, or other form described herein) may be provided with instructions for use together with a nicotinamide riboside powder. For example, both nicotinamide riboside and urolithin may be in powdered form.

Liquid compositions may be in the form of a medicine, in the form of a drink. Liquid formulations may be solutions, emulsions, slurries or other semi-liquids. Excipients in a liquid composition can, for example, provide a shelf-life, visual appearance, flavour and mouthfeel such that the composition has an acceptable taste, an attractive appearance and good storage stability. Liquid compositions may be provided for oral administration. Liquid compositions may be provided for topical application, for example in the form of creams, ointments or lotions.

For some uses, compositions of the invention may also be in the form of a solution suitable for injection or intravenous administration.

Additional Components in Compositions of the Invention:

The composition according to the invention may contain additional components beyond the urolithin and the nicotinamide riboside. The additional components may be compounds that provide health benefits, for example selected from vitamins, minerals, polyunsaturated fatty acids, functional amino acids and other compounds.

Amongst vitamins, there may specifically be mentioned Vitamin A, Vitamin C, Vitamin D, Vitamin E, Vitamin B12 and Vitamin K2. As used herein, "vitamin D" refers, to any of known form of vitamin D, and specifically includes vitamin D2 (ergocalciferol), vitamin D3 (cholecalciferol), vitamin D precursors, metabolites and other analogues, and combinations thereof, as well as the various active and inactive forms of vitamin D. For example, vitamin D3 may be provided in its unhydroxylated inactive form as cholecalciferol, or may be provided in its hydroxylated active form as calcitriol.

Creatine has been described as having beneficial effects in the treatment of muscle disorders. It can be included in compositions of the invention. $\beta$-hydroxyl-$\beta$-methylbutyrate (HMB) has been described as having beneficial effects in the treatment of muscle disorders. It can be included in compositions of the invention.

Amongst minerals, there may specifically be mentioned calcium salts (for example calcium phosphate), selenium, zinc salt, magnesium salts and iron salts.

For many muscle growth and/or muscle enhancement treatments, it is beneficial for certain particular amino acids to be provided. For example, L-arginine, L-glutamine, lysine and the branched-chain amino acids are considered important. These amino acids are sometimes known as "functional amino acids". The composition of the invention may include one or more branched-chain amino acids (leucine, isoleucine, and valine). The composition of the invention may include one or both of L-arginine and L-glutamine. The composition of the invention may include lysine.

Pharmaceutical compositions of the invention may include additional pharmaceutically active compounds. For example, a statin may be included. The invention may be provided as a kit comprising a composition of urolithin and nicotinamide riboside; and a pharmaceutically active compound, for example a statin.

A composition of the invention may include one or more further agents that are useful for mitochondrial biogenesis or the treatment of mitochondrial disorders. Such compounds include, without limitation, resveratrol, pyrroloquinoline quinone, ubiquinone, sulforaphane, co-enzyme Q10, genistein, hydroxyltyrosol, quercetin, L-carnitine, alpha-lipoic acid, and folinic acid (e.g., as leucovorin).

Additional compounds may further (or alternatively) be included in a composition of the invention, including for example tomatidine, ursolic acid, curcumin, capsaicin, menthol, trolamine salicylate and methylsalicylate.

In some exemplary embodiments, the compositions of the present disclosure may comprise, in addition to nicotinamide riboside and urolithin, one or more additional macronutrients, typically protein, fat or carbohydrate, or two or more of protein, fat and carbohydrate.

Any suitable source of fat or oil of the type commonly used in the preparation of foodstuffs and pharmaceuticals may be used in compositions of the invention. Non-limiting examples of suitable sources of fats for use in the compositions described herein also include polyunsaturated fatty acids such as docosahexaenoic acid (DHA), arachidonic acid (ARA), eicosapentaenoic acid (EPA) and combinations thereof.

Non-limiting examples of suitable carbohydrates or sources thereof for use in the compositions described herein may include maltodextrin, hydrolyzed or modified starch or cornstarch, glucose polymers, corn syrup, corn syrup solids, rice-derived carbohydrates, glucose, fructose, lactose, trehalose, high fructose corn syrup, tapioca dextrin, isomaltulose, sucromalt, maltitol powder, glycerin, fructooligosaccharides, soy fiber, corn fiber, guar gum, konjac flour, polydextrose, honey, sugar alcohols (e.g., maltitol, erythritol, sorbitol), and combinations thereof. Maltodextrin, sucrose and fructose are especially preferred.

Non-limiting examples of suitable proteins or sources thereof for use in the compositions described herein may include hydrolyzed, partially hydrolyzed or non-hydrolyzed proteins or protein sources. They may be derived from any known or otherwise suitable source such as milk (e.g., casein, whey), animal (e.g., meat, fish), cereal (e.g., rice, corn) or vegetable (e.g., soy, pea) sources. Combinations of sources or types of proteins may be used. Non-limiting examples of proteins or sources thereof include intact pea protein, intact pea protein isolates, intact pea protein concentrates, milk protein isolates, milk protein concentrates, casein protein isolates, casein protein concentrates, whey protein concentrates, whey protein isolates, sodium or calcium casemates, whole cow's milk, partially or completely defatted milk, yoghurt, soy protein isolates and soy protein concentrates, and combinations thereof. Combinations of sources or types of proteins may be used. For example, Greek- and Icelandic-style yoghurts are known to commonly have an especially high protein content which makes them especially suitable for use in formulations of the invention. Yoghurts for use in compositions of the invention may contain, for example, from 2 to 15 g of protein per 100 g. Particularly preferred are yoghurts with a high protein content, for example from 6 to 15 g per 100 g, for example from 7 to 15 g per 100 g, for example from 8 to 15 g per 100 g. Optionally, supplemental protein may also be added to a yoghurt formulation to increase the protein content of the formulation. Yoghurts of the invention may contain live cultures, such as *S. thermophilus, L. bulgaricus, L. acidophilus* or *L. lactis*.

The total concentrations or amounts of the protein, fat, carbohydrates and other components vary depending upon the nutritional needs of the intended user.

Additional components in a composition of the invention may be compounds that do not provide health benefits to the subject, but instead improve the composition in some other way, for example its taste, texture or shelf-life as mentioned above. The composition of the invention may thus further contain one or more compounds selected from emulsifiers, colorants, preservatives, gums, setting agents, thickeners, sweeteners and flavourings.

Suitable emulsifiers, colorants, preservatives, gums, setting agents and thickeners are well known in the art of manufacture of emulsions and other semi-liquids. For example preservatives, such as benzoic acid, sorbic acid, phosphoric acid, lactic acid, acetic acid, hydrochloric acid and the soluble salts thereof may be used.

A sweetener may be especially beneficial in a composition of the invention. High potency non-nutritive carbohydrate sweetening agents may be used, for example selected from aspartame, sucrose, potassium acelsufame, saccharin, cyclamates, Stevia, thaumatin and mixtures thereof. Aspartame is especially suitable.

A flavouring may be especially beneficial in a composition of the invention. In a liquid or semi-liquid composition, fruit flavour can be provided by inclusion of a fruit sauce or puree. Typical flavorings include strawberry, raspberry, blueberry, apricot, pomegranate, peach, pineapple, lemon, orange and apple. Generally, fruit flavorings include fruit extract, fruit preserve or fruit puree, with any of a combination of sweeteners, starch, stabilizer, natural and/or artificial flavors, colorings, preservatives, water and citric acid or other suitable acid to control the pH.

For oral preparations, the compositions can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compositions can be formulated into liquid preparations by dissolving, suspending or emulsifying them in an aqueous or nonaqueous solvent, such as vegetable or other similar oils, synthetic aliphatic acid glycerides, esters of higher aliphatic acids or propylene glycol; and if desired with conventional additives such as solubilizers, isotonic agents, suspending agents, emulsifying agents, stabilizers and preservatives. The compositions can be utilized in aerosol formulation to be administered via inhalation. They can be made into suppositories by mixing with a variety of bases such as emulsifying bases or water-soluble bases.

Unit dosage forms for oral administration such as syrups, elixirs, and suspensions may be provided wherein each dosage unit, for example, teaspoonful, tablespoonful, tablet or capsule, contains a predetermined amount of a composition of the invention. Similarly, unit dosage forms for injection or intravenous administration may comprise the compound of the present invention in a composition as a solution in sterile water, normal saline or another pharmaceutically acceptable carrier, wherein each dosage unit, for example, mL or L, contains a predetermined amount of a composition of the invention.

TABLE 1

Representative powder composition I:

| Composition | Per 100 g |
|---|---|
| Protein | 10-80 g |
| Carbohydrates | 20-40 g |
| Fat | 0-20 g |
| Polyunsaturated Fatty Acids | 0-5 g |
| Fiber | 0-5 g |
| Vitamins | 0-100% of respective RDAs |
| Minerals | 0-100% of respective RDAs |
| Folic Acid | 0-1000 µg |
| Niacin | 0-100 mg |
| Creatine | 0-20 g |
| Nicotinamide Riboside | 0.025-5 g |
| Urolithin A | 0.025-5 g |

TABLE 2

Representative powder composition II:

| Composition | Per 20 g |
|---|---|
| Vitamins | 0-100% of respective RDAs |
| Minerals | 0-100% of respective RDAs |
| Folic Acid | 0-1000 µg |

TABLE 2-continued

Representative powder composition II:

| Composition | Per 20 g |
| --- | --- |
| Niacin | 0-100 mg |
| Creatine | 0-2 g |
| Excipient filler | 0-4.5 g |
| Nicotinamide Riboside | 0.025-5 g |
| Urolithin A | 0.025-5 g |

Bulk powder is generally provided with instructions informing the subject how much of the powder to use for one serving. For example the bulk powder may be supplied in a container accompanied by a scoop of the necessary size to enable the correct amount of powder to be measured out. Powder may be taken neat, mixed with food, or added to water or a juice to make a drink.

TABLE 3

Representative drink composition I:

| Composition | Per 100 mL |
| --- | --- |
| Protein (for example 100% Hydrolyzed Whey) | 5-15 g |
| Carbohydrates | 1-20 g |
| Fat | 0-9.5 g |
| Polyunsaturated Fatty Acids | 0-2.5 g |
| Fiber | 0-2 g |
| Vitamins | 0-100% of respective RDAs |
| Minerals | 0-100% of respective RDAs |
| Folic Acid | 0-500 µg |
| Niacin | 0-20 mg |
| Nicotinamide Riboside | 0.025-5 g |
| Urolithin A | 10-5000 mg |

TABLE 4

Representative drink composition II:

| Composition | Per 30 mL |
| --- | --- |
| Vitamins | 0-100% of respective RDAs |
| Minerals | 0-100% of respective RDAs |
| Folic Acid | 0-500 µg |
| Niacin | 0-20 mg |
| Nicotinamide Riboside | 0.025-5 g |
| Urolithin A | 10-5000 mg |

TABLE 5

Representative bar composition I:

| Composition | Per bar of 35 g |
| --- | --- |
| Protein | 6.7 g |
| Carbohydrates | 10-20 g |
| Fat | 0-15 g |
| Polyunsaturated Fatty Acids | 2-6 g |
| Fiber | 0-5 g |
| Niacin | 0-100 mg |
| Vitamins | 0-100% of respective RDAs |
| Minerals | 0-100% of respective RDAs |
| L-Carnitine | 0-500 mg |
| Nicotinamide Riboside | 0.025-5 g |
| Urolithin A | 10-5000 mg |

TABLE 6

Representative bar composition II:

| Composition | Per bar of 35 g |
| --- | --- |
| Vitamins | 0-100% of respective RDAs |
| Minerals | 0-100% of respective RDAs |
| Niacin | 0-100 mg |
| L-Carnitine | 0-500 mg |
| Nicotinamide Riboside | 0.025-5 g |
| Urolithin A | 10-5000 mg |

TABLE 7

Representative yoghurt composition

| Composition | Per 100 g Yoghurt |
| --- | --- |
| Protein | 2-15 g |
| Carbohydrates | 3-20 g |
| Fat | 0-12 g |
| Calcium | 5-20% RDA |
| Fiber | 0-4 g |
| Vitamins | 0-100% of respective RDAs |
| Minerals | 0-100% of respective RDAs |
| Live Cultures | S. thermophilus, L. bulgaricus. L. acidophilus. L. lactis |
| Nicotinamide Riboside | 0.025-5 g |
| Urolithin A | 10-5000 mg |

The composition of the invention can be taken as a single treatment or, more commonly, as a series of treatments. In one example, a subject takes a dose before or after exercise. For a subject who is not able to exercise, a dose of the composition may, for example, be taken once, twice or three times per day, or one, two, three, four, five or six times per week. It will also be appreciated that the effective dosage of the compound may increase or decrease over the course of a particular treatment.

Treatments:

The compositions of the invention find use in improving muscle performance, improving muscle function, preventing a decline in muscle function, increasing muscle mass and/or reducing muscle wasting. The improvement in muscle performance, improving muscle function, the increase in muscle mass and/or reduction in muscle wasting may be as part of a medical treatment, or it may be for personal preference ("lifestyle") or cosmetic reasons, or as part of personal non-prescribed management of nutritional or physiological wellbeing. The compositions of the invention can be for use as a medicament. The compositions can be used as a dietary supplement, as a functional food, functional beverage, specialised nutrition or as a medical food.

The compositions find use in the treatment of both diseases and disease states. The compositions find use in the management normal physiological function in healthy individuals of conditions characterised by poor physical performance, impaired endurance capacity, and impaired muscle function. Compositions of the invention may improve physical performance in individuals with a disease, including young and elderly individuals. Compositions of the invention may improve physical performance, for example, short-term performance or long-term performance in healthy individuals, including athletes, non-athletic individuals, sedentary individuals and the elderly. This improvement of performance may be measured by the time spent to walk or run a certain distance (for example, an improved performance during the 6 minute walk test (MWT), an improved time to run a certain distance, an improved IPAQ score on the international physical activity questionnaire, an increased number of chair-stands in a certain time, or another test designed to measure physical performance.

The compositions also find use in the management and maintenance of normal physiological function (for example physical performance, endurance capacity and muscle function) in healthy individuals.

The compositions also find use in managing a nutritional state that leads to improved mitochondrial function. This is important, for example, in people having a disease or hospitalized, where the composition is administered not to treat a disease but as a nutritional supplement.

Compositions of the invention further provide for the improvement of endurance capacity. The endurance capacity refers to the time to fatigue when exercising at a constant workload, generally at an intensity <80% VO2max. Compositions of the invention may improve endurance capacity in individuals with a disease, including young and elderly individuals. Compositions of the invention may improve endurance capacity in healthy individuals, including athletes, non-athletic individuals, sedentary individuals and the elderly. The invention provides for a method of increasing the time to fatigue while performing a specific activity, for example, fitness training, walking, running, swimming, or cycling. This improvement of endurance capacity may be assessed with objective measurements (for example, speed, oxygen consumption or heart rate) or it can be self reported measurements (for example, using a validated questionnaire).

The invention further provides a composition to improve, maintain or reduce the loss of muscle function. Compositions of the invention may improve, maintain or reduce the loss of muscle function in individuals with a disease, including young and elderly individuals.

Compositions of the invention may improve, maintain or reduce the loss of muscle function in healthy individuals, including athletes, non-athletic individuals, sedentary individuals and the elderly. For example, compositions of the invention may improve, maintain or reduce the loss of muscle function in frail or pre-frail individuals. For example, compositions of the invention may increase muscle strength as evidenced by the improvement of performing a physical activity, such as an exercise, for example, increased ability to lift weights or increased hand grip strength. Also, compositions of the invention may improve muscle structure, for example by increasing or maintaining muscle mass in conditions of normal muscle function, declining muscle function or impaired muscle function.

This invention further provides a composition to improve the physical performance or endurance capacity as perceived by the individual. For example, by the reduction of in perceived exertion or effort during exercise or an activity as determined using a self-reported questionnaire.

Muscle Performance:

The composition of the invention is useful in enhancing muscle and/or physical performance. The invention thus provides a composition of the invention for use in enhancing muscle and/or physical performance. The invention also provides a method of enhancing muscle and/or physical performance by administering to a subject an effective amount of a composition of the invention. Administration can be self-administration.

The enhanced muscle performance may be one or more improved muscle function, reduced decline in muscle function, maintenance of muscle function, improved muscle strength, improved or maintenance of muscle endurance and improved muscle recovery.

The composition of the invention can thus be used in a method of improving physical endurance (e.g., ability to perform a physical task such as exercise, physical labor, sports activities), inhibiting or retarding physical fatigue, enhancing working capacity and endurance, and reducing muscle fatigue.

Improved muscle function can be particularly beneficial in elderly subjects with reduced muscle function as a result of an age-related condition, for example sarcopenia and muscle wasting. The composition of the invention may be used in enhancing muscle performance by administering a composition of the invention to a subject who is sedentary, frail or pre-frail.

Muscle performance may be sports performance, which is to say the ability of an athlete's muscles to perform when participating in sports activities. Enhanced sports performance, strength, speed, and endurance are measured by an increase in muscular contraction strength, increase in amplitude of muscle contraction, or shortening of muscle reaction time between stimulation and contraction. Athlete refers to an individual who participates in sports at any level and who seeks to achieve an improved level of strength, speed, or endurance in their performance, such as, for example, body builders, bicyclists, long distance runners, and short distance runners. Enhanced sports performance is manifested by the ability to overcome muscle fatigue, ability to maintain activity for longer periods of time, and have a more effective workout.

Medical Treatments:

The composition of the invention can be for use as a medicament. The compositions of the invention find use in the treatment of muscle-related pathological conditions. Accordingly, the invention provides a composition of the invention for use in the treatment of a muscle-related pathological condition. The invention also provides a method of treating a muscle-related pathological condition in a subject comprising administering to the subject an effective amount of a composition of the invention. Muscle-related pathological conditions include both conditions impacting generally healthy individuals as well as pathological conditions. Such muscle conditions found in healthy people or people affected by a disease include musculoskeletal diseases or disorders; cachexia; muscle wasting; myopathies; age-related decline in muscle function; pre-frailty; frailty; neuromuscular diseases, such as Duchenne muscular dystrophy and other dystrophies; sarcopenia, for example, acute sarcopenia; muscle atrophy and/or cachexia, for example muscle atrophy and/or cachexia associated with burns, bed rest, limb immobilization, or major thoracic, abdominal, and/or orthopedic surgery; multiple sclerosis, for example relapse remitting form thereof; and muscle degenerative disease.

Examples of age-related conditions that may be treated with compositions of the invention include sarcopenia, pre-frailty, frailty, swallowing difficulties or dysphagia, and muscle wasting. Generally, the compositions improve mitochondrial function associated with age-related decline in muscle function and/or mobility.

As mentioned above, the invention provides a composition comprising nicotinamide riboside and a compound of formula (I) or salts thereof for use as a medicament. For example, the medicament can be for use in the treatment of a disease or condition selected from the group consisting of metabolic syndrome, reduced metabolic rate, metabolic stress, cardiovascular disease, sarcopenia, muscle degenerative disease, inclusion body myositis (for example sporadic inclusion body myositis), Duchenne muscular dystrophy, alcoholic liver disease, nonalcoholic fatty liver disease (NAFLD), Nonalcoholic steatohepatitis (NASH), drug-induced liver injury, drug-induced cravings, anaemia disorders, α1-antitrypsin deficiency, ischemia/reperfusion injury, inflammation, inflammatory bowel disease, Crohn's disease, obesity, metabolic syndrome, type II diabetes mellitus, hyperlipidemia, osteoarthritis, neurodegenerative disease, Alzheimer's disease, Parkinson's disease, Huntington's disease, anxiety disorder, ulceration, amyotrophic lateral sclerosis, mitochondrial diseases (including for example poor growth, loss of muscle coordination, muscle weakness, visual problems, hearing problems, heart disease, liver disease, kidney disease, gastrointestinal disorders, respiratory disorders, neurological problems, autonomic dysfunction sometimes learning disabilities, and dementia as a result of mitochondrial disease. Further diseases related to mitochondrial dysfunction include: Diabetes mellitus and deafness (DAD); Leber's hereditary optic neuropathy (LHON); Leigh syndrome (subacute sclerosing encephalopathy); neuropathy, ataxia, retinitis pigmentosa, and ptosis (NARP); myoneurogenic gastrointestinal encephalopathy (MNGIE); Myoclonic Epilepsy with Ragged Red Fibers (MERRF); Mitochondrial myopathy, encephalomyopathy, lactic acidosis, stroke-like symptoms (MELAS); and mtDNA depletion) and cancer, cognitive disorder, stress, and mood disorder; for improving cognitive function; for weight management; or to increase muscle or mental performance. The compositions of the invention are particularly suitable for use in improving muscle function, muscle strength endurance and muscle recovery.

In particular, the invention provides compositions for use in the treatment of a disease or condition selected from the group consisting of metabolic syndrome, reduced metabolic rate, metabolic stress, cardiovascular disease, sarcopenia, pre-frailty, frailty, muscle degenerative disease, inclusion body myositis (for example sporadic inclusion body myositis), Duchenne muscular dystrophy, alcoholic liver disease, nonalcoholic fatty liver disease, drug-induced liver injury, drug-induced cravings, anaemia disorders, al-antitrypsin deficiency, ischemia/reperfusion injury, inflammation, inflammatory bowel disease, Crohn's disease, obesity, metabolic syndrome, type II diabetes mellitus, hyperlipidemia, osteoarthritis, neurodegenerative disease, Alzheimer's disease, Parkinson's disease, anxiety disorder, ulceration, amyotrophic lateral sclerosis, and cancer, cognitive disorder, stress, and mood disorder; for improving cognitive function; for weight management; or to increase muscle or mental performance.

The invention further provides compositions of the invention for use in the treatment of a disease or condition selected from the group consisting of metabolic stress, sarcopenia, muscle degenerative disease, inclusion body myositis (for example sporadic inclusion body myositis), Duchenne muscular dystrophy, alcoholic liver disease, nonalcoholic fatty liver disease, drug-induced liver injury, α1-antitrypsin deficiency, ischemia/reperfusion injury, inflammatory bowel disease, Crohn's disease, Alzheimer's disease, Parkinson's disease, amyotrophic lateral sclerosis, and cancer.

The invention further provides compositions of the invention for increasing autophagy or mitophagy in a cell. For example, the autophagy or mitophagy may be in embryonic stem cells, induced pluripotent stem cells, adult stem cells, differentiated cells, blood cells, hematopoietic cells, epithelial cells, exocrine cells, endocrine cells, connective tissue cells, adipose cells, bone cells, smooth muscle cells, striated muscle cells, nerve cells, sensory cells, cardiac cells, hepatic cells, gastric cells, intestinal cells, pulmonary cells, epidermal (i.e. skin) cells (including keratinocytes and fibroblasts), kidney cells, and germ cells. It may thus for example treat or prevent a disease or condition selected from the group consisting of metabolic syndrome, reduced metabolic rate, metabolic stress, cardiovascular disease, sarcopenia, muscle degenerative disease, inclusion body myositis (for example sporadic inclusion body myositis), Duchenne muscular dystrophy, alcoholic liver disease, nonalcoholic fatty liver disease, drug-induced liver injury, drug-induced cravings, anaemia disorders, α1-antitrypsin deficiency, ischemia/reperfusion injury, inflammation, inflammatory bowel disease, Crohn's disease, obesity, metabolic syndrome, type II diabetes mellitus, hyperlipidemia, osteoarthritis, neurodegenerative disease, Alzheimer's disease, Parkinson's disease, anxiety disorder, ulceration, amyotrophic lateral sclerosis, and cancer, cognitive disorder, stress, and mood disorder; or it can assist with weight management, or increase muscle or mental performance.

Amongst the neurodegenerative diseases, there may specifically be mentioned AIDS dementia complex, Alzheimer's disease, amyotrophic lateral sclerosis, adrenoleukodystrophy, Alexander disease, Alper's disease, ataxia telangiectasia, Batten disease, bovine spongiform encephalopathy (BSE), Canavan disease, corticobasal degeneration, Creutzfeldt-Jakob disease, dementia with Lewy bodies, fatal familial insomnia, frontotemporal lobar degeneration, Huntington's disease, Kennedy's disease, Krabbe disease, Lyme disease, Machado-Joseph disease, multiple sclerosis, multiple system atrophy, neuroacanthocytosis, Niemann-Pick disease, Parkinson's disease, Pick's disease, primary lateral sclerosis, progressive supranuclear palsy, Refsum disease, Sandhoff disease, diffuse myelinoclastic sclerosis, spinocerebellar ataxia, subacute combined degeneration of spinal cord, tabes dorsalis, Tay-Sachs disease, toxic encephalopathy, transmissible spongiform encephalopathy, and wobbly hedgehog syndrome. In one embodiment, the neurodegenerative disease is selected from the group consisting of Alzheimer's disease, amyotrophic lateral sclerosis, Huntington's disease, and Parkinson's disease. In one embodiment, the neurodegenerative disease is Alzheimer's disease.

An aspect of the invention is in improving cognitive function. In one embodiment, the cognitive function is selected from the group consisting of perception, memory, attention, speech comprehension, speech generation, reading comprehension, creation of imagery, learning, and reasoning. In one embodiment, the cognitive function is selected from the group consisting of perception, memory, attention, and reasoning. In one embodiment, the cognitive function is memory.

An aspect of the invention is in the treatment of stress-induced or stress-related cognitive deficit. An aspect of the invention is in the treatment of a mood disorder. In one embodiment, the mood disorder is selected from the group consisting of depression, postpartum depression, dysthymia, and bipolar disorder. In one embodiment, the mood disorder is depression. In one embodiment, the mood disorder is dysthymia.

An aspect of the invention is in the treatment of stress-induced or stress-related mood disorder, e.g., dysthymia. An aspect of the invention is in the treatment of an anxiety disorder. In one embodiment, the anxiety disorder is selected from the group consisting of generalized anxiety disorder, panic disorder, panic disorder with agoraphobia, agoraphobia, social anxiety disorder, obsessive-compulsive disorder, and post-traumatic stress disorder. In one embodiment, the anxiety disorder is generalized anxiety disorder. In one embodiment, the anxiety disorder is post-traumatic stress disorder.

An aspect of the invention is in the treatment of stress-induced or stress-related anxiety.

An aspect of the invention is in the treatment of a muscle or neuromuscular disease. In one embodiment, the muscle or neuromuscular disease is a myopathy. In one embodiment, the muscle or neuromuscular disease is sarcopenia. In one embodiment, the muscle or neuromuscular disease is a muscular dystrophy. In one embodiment, the muscle or neuromuscular disease is Duchenne muscular dystrophy. In one embodiment, the muscle or neuromuscular disease is inclusion body myositis, for example sporadic inclusion body myositis.

An aspect of the invention is in the treatment of mitochondrial disease. For example, a subject may require treatment of loss of muscle coordination, muscle weakness, visual problems, hearing problems, heart disease, liver disease, kidney disease, gastrointestinal disorders, respiratory disorders, neurological problems, autonomic dysfunction sometimes learning disabilities, and dementia as a result of mitochondrial disease.

An aspect of the invention is in enhancing muscle performance. In one embodiment, the muscle performance is selected from the group consisting of strength, speed, endurance and recovery. In humans, muscle function generally declines with age starting during the third decade of life; the decline generally accelerates after age 65. An aspect of the invention is thus in maintaining muscle performance during the aging process. The enhancement of muscle performance may be as part of the use of the compounds in sports nutrition, in aiding healthy aging (for example from age 45 to 65), and in slowing the rate of muscle decline in those aged over 65 (pre-frail)

Uses:

The compositions of the invention also find use in in vitro testing of treatments for particular conditions.

BRIEF DESCRIPTION OF THE DRAWINGS

FIG. 1A is the heatmap representing the intensities of the bands shown on FIG. 1B.

FIG. 2 represents the mitochondrial respiratory subunits and autophagy gene expression results in C2C12 myoblasts after DMSO for 24 hours, 0.1 µM UA for 24 hours, 1 mM NR for 6 hours, or 0.1 µM UA for 24 hours and 1 mM NR for 6 hours. FIG. 3 represents the mitochondrial respiratory subunits and autophagy gene expression results in C2C12 myoblasts after DMSO for 24 hours, 1 µM UA for 24 hours, 1 mM NR for 6 hours, or 1 µM UA for 24 hours and 1 mM NR for 6 hours. FIG. 4 represents the mitochondrial respiratory subunits and autophagy gene expression results in C2C12 myoblasts after DMSO for 24 hours, 25 µM UA for 24 hours, 1 mM NR for 24 hours, or 24 µM UA and 1 mM NR for 24 hours.

EXAMPLES

Figure 1:
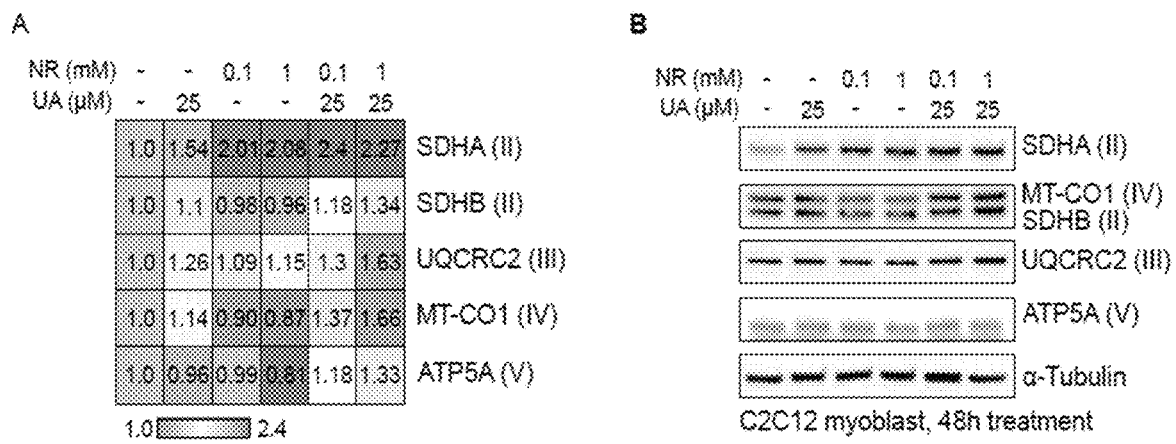
FIG. 1 shows the results of Example 6, specifically the quantification of mitochondrial respiratory subunits proteins in C2C12 myoblasts after 48 hours of treatment with DMSO (control), UA, NR or the combination of UA and NR.

The following Examples illustrate the invention.

Example 1: Compounds

Urolithin A was prepared as follows:

Urolithin A (4) was prepared in two steps starting from bromide 1 and resorcinol 2. The pure compound was obtained as a pale yellow powder.

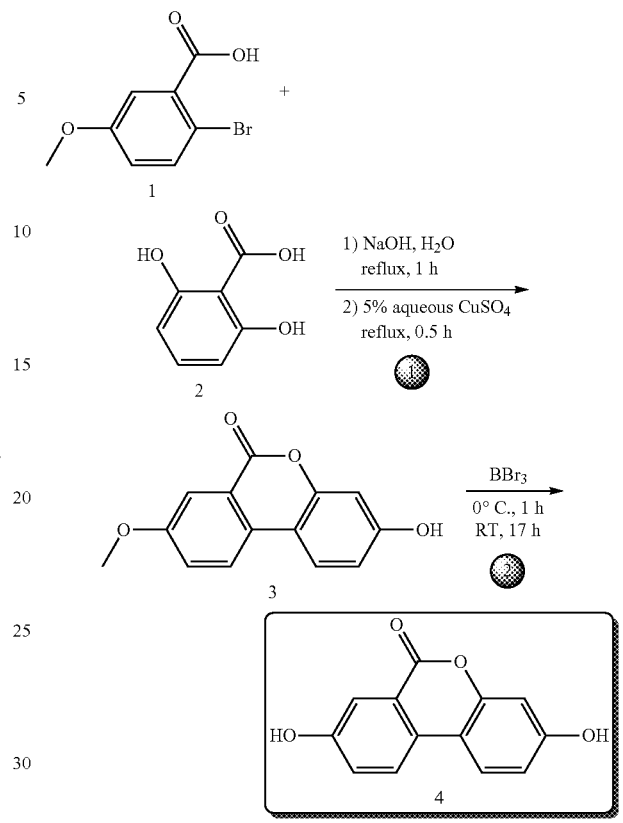

Step 1:

A mixture of 2-bromo-5-methoxybenzoic acid 1 (27.6 g; 119 mmol; 1.0 eq.), resorcinol 2 (26.3 g; 239 mmol; 2.0 eq.) and sodium hydroxide (10.5 g; 263 mmol; 2.2 eq.) in water (120 mL) was heated under reflux for 1 hour. A 5% aqueous solution of copper sulphate (3.88 g of $CuSO_4.5H_2O$ in 50 mL water; 15.5 mmol; 0.1 eq.) was then added and the mixture was refluxed for an additional 30 minutes. The mixture was allowed to cool to room temperature and the solid was filtered on a Büchner filter. The residue was washed with cold water to give a pale red solid which was triturated in hot MeOH. The suspension was left overnight at 4° C. The resultant precipitate was filtered and washed with cold MeOH to yield the title compound 3 as a pale brown solid.

Step 2:

To a suspension of 3 (10.0 g; 41 mmol; 1.0 eq.) in dry dichloromethane (100 mL) was added dropwise at 0° C. a 1 M solution of boron tribromide in dry dichloromethane (11.93 mL of pure BBr3 in 110 mL of anhydrous dichloromethane; 124 mmol; 3.0 eq.). The mixture was left at 0° C. for 1 hour and was then allowed to warm up to room temperature. The solution was stirred at that temperature for 17 hours. Then ice was added thoroughly to the mixture. The yellow precipitate was filtered and washed with cold water to give a yellow solid which was heated to reflux in acetic acid for 3 hours. The hot solution was filtered quickly and the precipitate was washed with acetic acid, then with diethyl ether to yield the title compound 4 as a yellow solid. $^1H$ and $^{13}C$ NMR were in accordance with the structure of 4.

Example 2: Powder Formula Composition Targeting Healthy Aging and Age-Related Muscle Loss Containing High Protein, Nicotinamide Riboside and Urolithin A

TABLE 8

| Composition | Per 100 g (single serving) |
|---|---|
| Protein | 51.5 g |
| Whey | (45 g) |
| Leucine | (3.5 g) |
| Isoleucine | (1.5 g) |
| L-Arginine | (1.5 g) |
| Carbohydrates | 28 g |
| Fat | 11.5 g |
| Polyunsaturated Fatty Acids | 2.5 g |
| Fiber | 2.0 g |
| Vitamin A | 50 µg |
| Vitamin D3 | 50 µg |
| Vitamin E | 20 mg |
| Vitamin C | 100 mg |
| Vitamin B6 | 2 mg |
| Vitamin B12 | 10 µg |
| Folic Acid | 500 µg |
| Niacin | 50 mg |
| Zinc | 5 mg |
| Calcium | 100 mg |
| Selenium | 40 µg |
| Iron | 20 mg |
| Magnesium | 100 mg |
| Creatine | 1.5 g |
| Urolithin A | 500 mg |
| Nicotinamide Riboside | 500 mg |

The compositon with the nutrient profile shown in Table 8 is given to a subject to counteract age related muscle loss.

Example 3: An Enteral Nutrition Liquid Composition Targeting Immobilized Subject in Intensive Care or Hospital Settings Containing Nicotinamide Riboside and Urolithin A

TABLE 9

| Composition | Per 100 mL |
|---|---|
| Protein | 10.5 g |
| 100% Hydrolyzed Whey | |
| Carbohydrates | 15.4 g |
| Fat | 9.9 g |
| Polyunsaturated Fatty Acids | 3.8 g |
| Fiber | 0 g |
| Vitamin A | 170 µg |
| Vitamin D3 | 2 µg |
| Vitamin E | 3 mg |
| Vitamin C | 20 mg |
| Vitamin B6 | 0.3 mg |
| Vitamin B12 | 1 µg |
| Folic Acid | 50 µg |
| Niacin | 5 mg |
| Zinc | 1.5 mg |
| Calcium | 100 mg |
| Selenium | 10 µg |
| Iron | 2 mg |
| Magnesium | 40 mg |
| Urolithin A | 500 mg |
| Nicotinamide Riboside | 500 mg |

The drink compositon with the nutrient profile shown in Table 9 is given to an immobilised subject in intensive care or a hospital setting.

Example 4: A Cereal Bar Composition Targeting an Active Athlete for Optimal Muscle Function During Endurance Training Containing Nicotinamide Riboside and Urolithin A

TABLE 10

| Composition | Per bar of 35 g |
|---|---|
| Energy | 600 kcal |
| Protein | 6.7 g |
| Carbohydrates | 17.2 g |
| Fat | 7.6 g |
| Polyunsaturated Fatty Acids | 3.8 g |
| Fiber | 1.6 g |
| Niacin | 25 mg |
| Zinc | 2.5 mg |
| Calcium | 180 mg |
| Sodium | 25 mg |
| Potassium | 60 mg |
| Magnesium | 80 mg |
| L-Carnitine | 200 mg |
| Urolithin A | 500 mg |
| Nicotinamide Riboside | 500 mg |

The bar compositon with the nutrient profile shown in Table 10 is given to an active athlete for optimal muscle function during endurance.

Example 5: A Yogurt Composition

TABLE 11

| Nutrition value: | per 100 g | |
|---|---|---|
| Fat | 0.2 g | |
| Carbohydrates | 3.7 g | |
| Protein | 9.8 g | |
| Vitamin B2 | 0.18 mg | 13% of RDA |
| Calcium | 95 mg | 12% of RDA |
| Phosphorus | 170 mg | 24% of RDA |
| Live Active Cultures | | |
| Urolithin A | 100 mg, 250 mg, 500 mg, 750 mg or 1000 mg | |
| Nicotinamide Riboside | 250 mg, 500 mg, 1000 mg, 2000 mg, 3000 mg | |

Example 6: In Vitro Testing of Urolithin A and Nicotinamide Riboside on Mitochondrial Respiratory Subunits Proteins in Muscle Cells C2C12 myoblasts were cultured in Dulbecco's modified Eagle's medium (DMEM) including 4.5 g/L glucose, 10% fetal calf serum, and 50 µg/mL gentamicin. Urolithin A (UA) was dissolved in DMSO in a stock solution of 50 mM. Nicotinamide riboside (NR) in the form of the triflate salt was dissolved in double-distilled water in a stock solution of 1 M. One hundred thousand cells were plated at time 0 hours in 6-wells plates. A total of 3 wells was used per condition (n=3 per group). Cells were treated in a volume of 2 ml for a period of 48 hours at final concentrations of (a) DMSO 0.1%, (b) 25 µM UA, (c) 0.1 mM NR, (d) 1 mM NR, (e) 25 µM UA+0.1 mM NR and (f) 25 µM UA+1 mM NR.

At the end of the treatment, cells were lysed with cell lysis buffer (#9803, Cell signalling) containing protease (cOmplete™, Roche) and phosphatase inhibitor (PhosSTOP™, Roche) and applied to Invitrogen NuPage® Novex® Gel System (Bis-Tris Protein Gels—4-12%, Thermo fisher Scientific). Protein levels were examined for mitochondrial respiratory subunits, including mitochondrially encoded cytochrome c oxidase I (MTCO1), succinate dehydrogenase complex flavoprotein subunit A (SDHA) and B (SDHB), ubiquinol-cytochrome c reductase core protein II (UQCRC2) and ATP synthase, H+ transporting, mitochondrial F1 complex, alpha subunit 1 (ATP5A). The housekeeping protein tubulin-α was measured as a loading control. Detection of the proteins was performed using an Azure c300 (Azure biosystem) (FIG. 1B). Western Blot images were representative of the three biological replicates. Experiments were repeated at least 2 times. Bands were quantified using ImageJ software. The heatmap of the band intensities was drawn using GEN-E (Broad Institute) conditional formatting. Control DMSO values were set to one (FIG. 1A).

As shown in FIG. 1, UA at 25 µM alone induces an increase in SDHA (+54%), SDHB (+10%), UQCRC2 (+26%) and MT-CO1 (+14%) proteins levels, while no change is observed in ATP5A protein levels. NR has a different effect, which is not dose-dependent at the tested concentrations. Both NR 0.1 and 1 mM lead to a +≈100% increase in SDHA, no change in SDHB, +≈10% in UQCRC2 and −≈10% in MT-CO1. NR at 0.1 mM has no effect on ATP5A while NR at 1 mM decreases it by 20%. In contrast, the combination of UA and NR increases all protein levels, and to higher extent than with the single compounds. UA 25 µM+NR 0.1 mM increase SDHA by 140%, SDHB by +18%, UQCRC2 by +30%, MT-CO01 by 37% and ATP5A by 18% while UA 25 µM+NR 1 mM increase SDHA by 127%, SDHB by +34%, UQCRC2 by +63%, MT-CO1 by 66% and ATP5A by 33%.

These results show that the combination of UA and NR has a synergistic effect on mitochondrial biogenesis, and this effect is conserved across several concentrations of NR. Interestingly, there is a dose-dependent effect with NR when combined with UA, while it is not the case with the compound alone.

Example 7: In Vitro Testing of Urolithin A and Nicotinamide Riboside on Mitochondrial Biogenesis and Autophagy Markers Expression in Muscle Cells C2C12 myoblasts were cultured in Dulbecco's modified Eagle's medium (DMEM) including 4.5 g/L glucose, 10% fetal calf serum, and 50 µg/mL gentamicin. Urolithin was dissolved in DMSO in a stock solution of 50 mM. Nicotinamide riboside in the form of the triflate salt was dissolved in double-distilled water in a stock solution of 1 M. One hundred thousand cells were plated at time 0 hours in 6-wells plates. A total of 6 wells was used per condition (n=6 per group).

Figure 2:
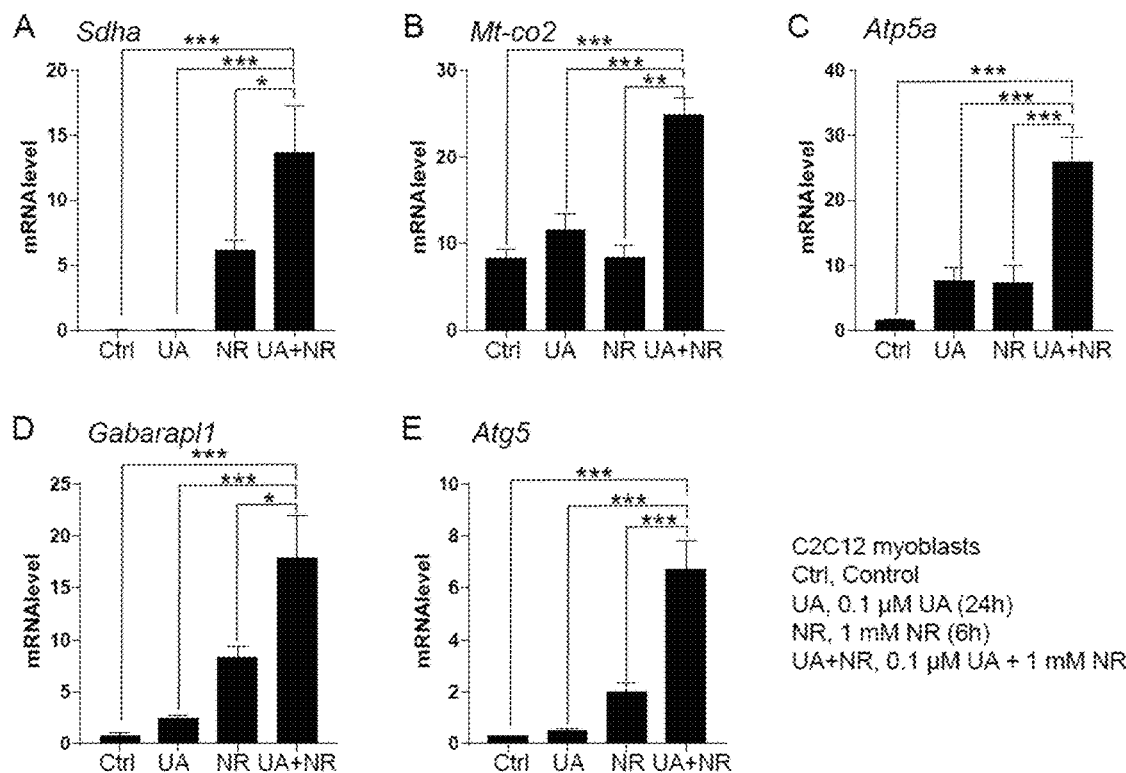
FIGS. 2, 3 and 4 show the results of Example 7. Specifically.
Figure 3:
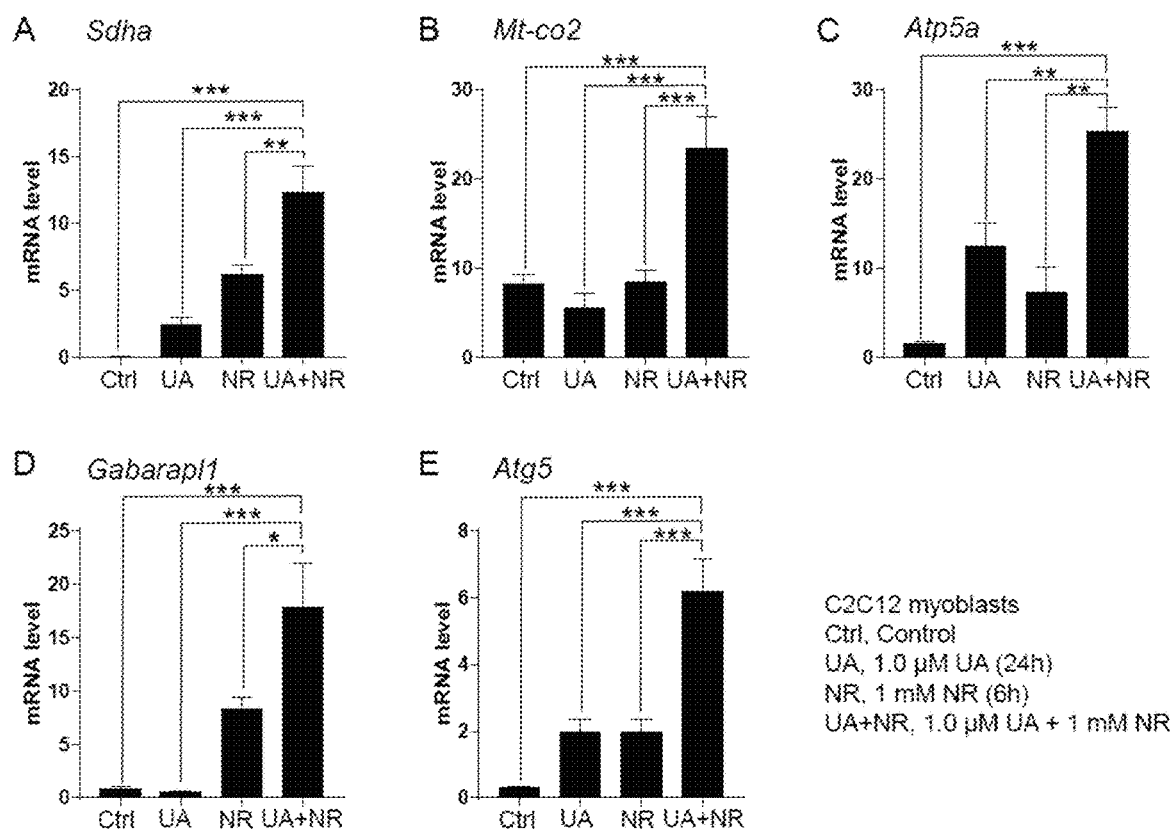

In a first batch of experiments, cells were treated in a volume of 2 ml with (a) DMSO 0.1% for 24 hours, (b) 0.1 µM UA for 24 hours, (c) 1 µM UA for 24 hours, (d) 1 mM NR for 6 hours, (e) 0.1 µM UA for 24 hours and 1 mM NR for 6 hours, (f) 1 µM for 24 hours and 1 mM NR for 6 hours (FIGS. 2 and 3)

Figure 4:
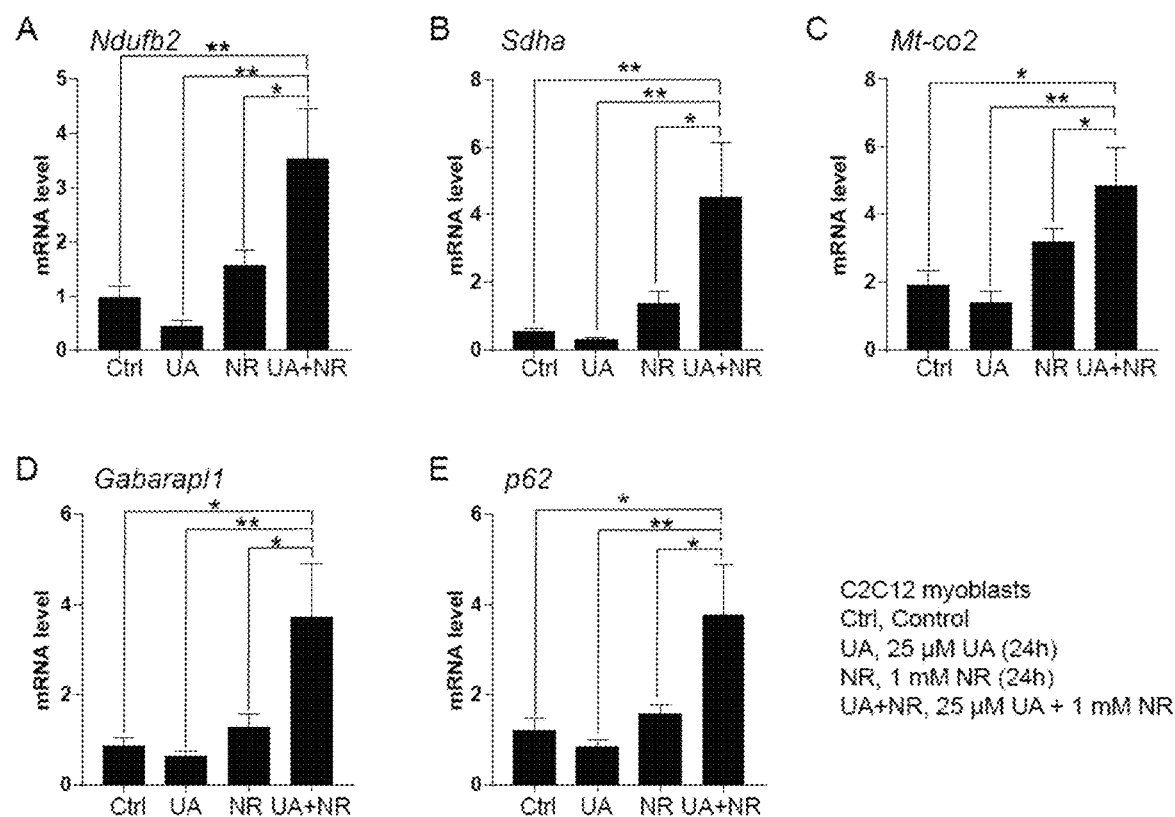

In a second batch of experiments, cells were treated in a volume of 2 ml with (a) DMSO 0.1% for 24 hours, (b) 25 µM UA for 24 hours, (d) 1 mM NR for 24 hours, and (e) 25 µM UA and 1 mM NR for 24 hours (FIG. 4).

At the end of treatment, total RNA was prepared using TRIzol (Invitrogen). cDNA was prepared using the QuantiTect Reverse Transcription Kit (Qiagen) following the manufacturer's instructions. The RT-qPCR reactions were performed using the Light-Cycler system (Roche Applied Science) and a qPCR Supermix (Qiagen) with the indicated primers (Table 12). Genes that belong to mitochondrial biogenesis pathway (succinate dehydrogenase complex flavoprotein subunit A, SDHA; mitochondrially encoded cytochrome c oxidase II, MT-CO2; ATP synthase, H+ transporting, mitochondrial F1 complex, alpha subunit 1, ATP5A and NADH:ubiquinone oxidoreductase subunit B2, NDUFB2) and autophagy pathway (Autophagy related 5, ATG5; GABA type A receptor associated protein like 1, GABARAPL1 and sequestosome 1, p62) were analysed and normalized over the housekeeping genes actin beta (ACTB) and hypoxanthine phosphoribosyltransferase 1 (HPRT1). FIG. 2 shows the combination of UA at 0.1 µM for 24 hours with NR at 1 mM for 6 hours, while FIG. 3 shows the combination of UA at 1 µM for 24 hours with NR at 1 mM for 6 hours. FIG. 4 shows the combination of UA at 25 µM with NR at 1 mM for 24 hours. Bargraphs represent mean±SEM. *P<0.05; P<0.01; *P<0.001 is for the statistical difference between the combination of UA and NR and other treatments after one-way ANOVA followed by Bartlett's test and Dunnett's multiple comparisons test. Experiments were repeated at least 2 times.

As shown in FIGS. 2 and 3, the combination of UA 0.1 or 1 µM 24 hours and NR 1 mM 6 hours leads to a significantly higher increase of mitochondrial respiratory subunits (FIG. 2A-C and FIG. 3A-C) and autophagy genes (FIGS. 2D-E and 3D-E) than with UA alone or NR alone. Likewise, the combination of UA 25 µM and NR 1 mM for 24 hours induces significantly more mitochondrial biogenesis (FIG. 4A-C) and autophagy genes (FIG. 4D-E) than with UA alone or NR alone. These results show that the combination of UA and NR has a synergistic effect on mitochondrial biogenesis and autophagy, and this effect is conserved across several concentrations of UA and several treatment timings of NR. These results are surprising as both mitochondrial biogenesis and autophagy genes are upregulated upon the combination of urolithin A and nicotinamide riboside.

The primers used for the RT-qPCR analyses were the literature primers known from the references indicated in the Table 12 below.

TABLE 12

| Gene | Gene ID | Reference |
| --- | --- | --- |
| Actb | 11461 | Ryu et al., Nature Medicine 2016, 22 (8):879-88 (Pubmed ID 27400265) |
| Hprt1 | 15452 | Hruz et al., BMC Genomics. 2011; 12:156. (Pubmed ID 21418615) |
| SDHA | 66945 | Al-Sawaf et al., Sci Rep. 2014; 4:3625. (Pubmed ID 24406502) |
| MT-CO2 | 17709 | Gaignard et al., Endocrinology, 2015, 156 (8), pp. 2893-2904, also; Ryu et al |
| ATP5A | 11946 | Mohamed et al., J Transl Med. 2016; 14: 149. (Pubmed ID 27234427) |
| NDUFB2 | 68198 | Hwang et al, Biochemistry, 2015, 54 (24), pp 3739-3748 (Pubmed ID 26030260) |
| GABARAPL1 | 57436 | Lee and Goldberg, J Biol Chem. Dec. 18, 2015; 290(51): 30269-30279 (PMCID 4683253), also; Ryu et al |
| p62 | 18412 | Ryu et al., Nature Medicine 2016, 22 (8):879-88 (Pubmed ID 27400265) |
| Atg5 | 11793 | Ryu et al., Nature Medicine 2016, 22 (8):879-88 (Pubmed ID 27400265) |

Example 8a: In Vitro Testing of Urolithin a and Nicotinamide Riboside on Autophagy and Mitochondrial Biogenesis in Muscle Cells C2C12 myoblast are cultured in Dulbecco's modified Eagle's medium (DMEM) including 4.5 g/L glucose, 20% fetal calf serum, and 50m/mL gentamicin. Urolithin is dissolved in DMSO in a stock solution of 50 mM. Nicotinamide riboside is dissolved in DMSO in a stock solution of 50 mM. Cells are treated at final concentrations of 50 µM urolithin, 1 mM nicotinamide riboside, or 50 µM urolithin and 1 mM nicotinamide riboside for a period 24 hours. Control cells are treated with DMSO at an equivalent final concentration for the same period and serves as the untreated control.

Human primary skeletal myocytes are cultured in vitro and exposed to concentrations of 50 µM urolithin, 1 mM nicotinamide riboside, or 50 µM urolithin and 1 mM nicotinamide riboside for 24 hours. Human skeletal myoblasts are grown in DMEM plus 2% horse serum. Control cells are treated with DMSO at an equivalent final concentration for the same period and served as the untreated control.

At the end of treatment, RNA is extracted from the cells and converted to cDNA for qPCR analysis. Genes that belong to NAD+ synthesis pathway (Nampt), mitochondrial biogenesis pathway (Pgc1α, Sirt1, Nrf1, Tfam, Mrps5), mitochondrial respiratory chain subunits (Ndufb5, Sdha, CytC, CoxIV, Atp5 g1), autophagy pathway (LC3B, Pik3c3, p62, Gabarapl1) and mitophagy pathway (Parkin, PINK1) are analysed and normalized over the housekeeping genes Actb and Hprt1. The results show the effect of urolithin A combined with nicotinamide riboside on the expression of genes belonging to NAD+ synthesis pathway, mitochondrial biogenesis and respiratory subunits, autophagy and mitophagy.

Also, at the end of the treatment, cells are lysed with RIPA buffer and applied to SDS-PAGE and protein levels are examined for autophagy-related proteins (LC3-I and LC3-II, p62, AMPKa, and p-AMPKa), mitophagy related protein (Parkin), mitochondrial respiratory subunits (MTCO1, NDUFS3, SDHA, SDHB, UQCRC2, ATP5A). The housekeeping protein for total protein load β-actin is measured as a loading control. The mitochondrial protein VDAC1 is used as a housekeeping protein for mitochondrial abundance. The results show the effect of the urolithins A combined with nicotinamide riboside on the level of autophagy, mitophagy and mitochondrial abundance in the cells in question.

Example 8b: In Vitro Testing of Urolithin a and Nicotinamide Riboside on Respiratory Capacity in Muscle Cells C2C12 myoblast are cultured in Dulbecco's modified Eagle's medium (DMEM) including 4.5 g/L glucose, 20% fetal calf serum, and 50 µg/mL gentamicin. Urolithin is dissolved in DMSO in a stock solution of 50 mM. Nicotinamide riboside is dissolved in DMSO in a stock solution of 50 mM. Cells are treated at final concentrations of 50 µM urolithin, 1 mM nicotinamide riboside, or 50 µM urolithin and 1 mM nicotinamide riboside for a period 24 hours. Control cells are treated with DMSO at an equivalent final concentration for the same period and serves as the untreated control.

Human primary skeletal myocytes are cultured in vitro and exposed to concentrations of 50 µM urolithin, 1 mM nicotinamide riboside, or 50 µM urolithin and 1 mM nicotinamide riboside for 24 hours. Human skeletal myoblasts are grown in DMEM plus 2% horse serum. Control cells are treated with DMSO at an equivalent final concentration for the same period and served as the untreated control.

At the end of the treatment, respiratory capacity is determined by measuring basal oxygen consumption and following the additions of the uncoupler Carbonyl cyanide m-chlorophenyl hydrazine (CCCP) at a final concentration of 10 µM. The results show the effect of urolithin A combined with nicotinamide riboside on respiratory capacity in the cells in question.

Example 8c: Experimental Trial on Muscle Function 22 month old C57BL/6J old mice that would be equivalent to a 65 yr to 75 yr old elderly human are used in a model of aging. The mice are treated with (i) diet without any supplement, (ii) diet supplemented with urolithin, (iii) diet supplemented with nicotinamide riboside; or (iv) diet supplemented with urolithin and nicotinamide riboside. In addition to the supplements, the diets contain protein, fat, carbohydrate essential nutrients, vitamins and minerals.

At the end of the treatment with the diet, muscles are weighed and collected. RNA is extracted from the cells and converted to cDNA for qPCR analysis. Genes that belong to NAD+ synthesis pathway (Nampt), mitochondrial biogenesis pathway (Pgc1α, Sirt1, Nrf1, Tfam, Mrps5), mitochondrial respiratory chain subunits (Ndufb5, Sdha, CytC, CoxIV, Atp5 g1), autophagy pathway (LC3B, Pik3c3, p62, Gabarapl1) and mitophagy pathway (Parkin, PINK1) are analysed and normalized over the housekeeping genes Actb and Hprt1. The results show the effect of urolithin A combined with nicotinamide riboside on the expression of genes belonging to NAD+ synthesis pathway, mitochondrial biogenesis and respiratory subunits, autophagy and mitophagy.

The invention claimed is:

1. A method of improving, maintaining, enhancing, increasing, or promoting mitochondrial function or activity, comprising administering to a subject in need thereof an effective amount of a composition comprising:
    a) nicotinamide riboside; and
    b) urolithin A or a salt thereof;
        wherein the nicotinamide riboside is present in an amount of 20 mg to 5 g; and the urolithin A is present in an amount of 10 mg to 5 g.

2. The method of claim 1, wherein the composition is formulated as a solid, a semi-solid, a powder, or a liquid.

3. The method of claim 1, wherein the composition is formulated as a medicament, dietary supplement, functional food, functional beverage, specialized nutrition, or medical food.

4. The method of claim 1, wherein mitochondrial function or activity is improved.

5. The method of claim 1, wherein mitochondrial function or activity is maintained.

6. The method of claim 1, wherein mitochondrial function or activity is enhanced.

7. The method of claim 1, wherein mitochondrial function or activity is increased.

8. The method of claim 1, wherein mitochondrial function or activity is promoted.

9. The method of claim 1, wherein mitochondrial biogenesis is increased.

10. The method of claim 1, wherein physical endurance is improved, physical fatigue is inhibited or reduced, blood oxygen levels are enhanced, energy in healthy individuals is enhanced, working capacity and endurance is enhanced, muscle fatigue is reduced, muscle ATP levels are increased, or lactic acid in blood is reduced.

* * * * *